(12) United States Patent
Xiao

(10) Patent No.: US 10,881,147 B2
(45) Date of Patent: Jan. 5, 2021

(54) E-LIQUID PUMPING ASSEMBLY AND ELECTRONIC CIGARETTE

(71) Applicant: SHENZHEN UWELL TECHNOLOGY CO., LTD., Shenzhen (CN)

(72) Inventor: Yucheng Xiao, Shenzhen (CN)

(73) Assignee: SHENZHEN UWELL TECHNOLOGY CO., LTD., Shenzhen (CN)

( * ) Notice: Subject to any disclaimer, the term of this patent is extended or adjusted under 35 U.S.C. 154(b) by 350 days.

(21) Appl. No.: 16/019,567

(22) Filed: Jun. 27, 2018

(65) Prior Publication Data

US 2019/0364965 A1     Dec. 5, 2019

(30) Foreign Application Priority Data

Jun. 4, 2018   (CN) .................. 2018 2 08522624 U

(51) Int. Cl.
| | | |
|---|---|---|
| *A24F 13/00* | (2006.01) | |
| *A24F 47/00* | (2020.01) | |
| *A61M 11/00* | (2006.01) | |
| *A61M 11/04* | (2006.01) | |

(52) U.S. Cl.
CPC ......... *A24F 47/008* (2013.01); *A61M 11/007* (2014.02); *A61M 11/042* (2014.02); *A61M 2205/8206* (2013.01)

(58) Field of Classification Search
CPC ................................ A24F 47/00; A61M 11/07
USPC ................................................. 131/328, 329
See application file for complete search history.

(56) References Cited

U.S. PATENT DOCUMENTS

| | | | |
|---|---|---|---|
| 2013/0199528 A1* | 8/2013 | Goodman | A24F 47/008 128/203.26 |
| 2015/0114409 A1* | 4/2015 | Brammer | A24F 47/008 131/329 |
| 2015/0216237 A1* | 8/2015 | Wensley | A24F 40/46 131/273 |

* cited by examiner

*Primary Examiner* — Phuong K Dinh

(57) ABSTRACT

An e-liquid pumping assembly for supplying e-liquid to an atomizer includes a housing, an e-liquid bottle, and a pumping head assembly. The pumping head assembly includes a piston, a pumping body clamped with the e-liquid bottle by a first sealing portion, a pumping cover clamped with the pumping body, a feeding tube connected to the atomizer and the pumping body. The piston includes a first lower end inserted into the pumping body and a first upper end exposed from the pumping cover. The e-liquid suction pipe includes a second lower and upper ends respectively inserted into the e-liquid bottle and the pumping body. The piston is pressed to expel air from the pumping body so that e-liquid enters the pumping body through the e-liquid suction pipe. The piston is again pressed for pushing the e-liquid out of die pumping body to the atomizer through the feeding tube.

18 Claims, 9 Drawing Sheets

E-LIQUID PUMPING ASSEMBLY AND ELECTRONIC CIGARETTE

BACKGROUND

1. Technical Field

The present disclosure generally relates to electronic cigarettes field, and especially relates to an e-liquid pumping assembly supplying e-liquid to an atomizer of an electronic cigarette and an electronic cigarette thereof.

2. Description of Related Art

E-liquid in a conventional electronic cigarette is pumped by squeezing an e-liquid bottle of the electronic cigarette, thereby the e-liquid can't be completely pumped clean. In addition, the e-liquid bottle is connected to a pumping head assembly of the electronic cigarette by threads, which is inconveniently assembly or disassembly the electronic cigarette.

SUMMARY

The technical problems to be solved: in view of the shortcomings of the related art, the present disclosure relates to an e-liquid pumping assembly and an electronic cigarette thereof which has a simple structure to be conveniently disassembled and assembled.

The technical solution adopted for solving technical problems of the present disclosure is:

An e-liquid pumping assembly for supplying e-liquid to an atomizer includes a housing, an e-liquid bottle and a pumping head assembly respectively received in the housing. The pumping head assembly includes a piston, a pumping body clamped with the e-liquid bottle by a first sealing portion, a pumping cover clamped with the pumping body, a feeding tube connected to the atomizer and clamped with the pumping body and an e-liquid suction pipe. The piston includes a first upper end exposed outward from the pumping cover and a first lower end inserted into the pumping body. The e-liquid suction pipe includes a second upper end inserted into the pumping body and a second lower end inserted into the e-liquid bottle. The piston is pressed to expel air from the pumping body so that e-liquid can enter the pumping body through the e-liquid suction pipe; while the piston is again pressed for pushing the e-liquid out of the pumping body to enter the atomizer through the feeding tube.

Wherein the pumping body includes a first portion, a second portion opposite to the first portion and a receiving room passing through the first portion and the second portion, the pumping cover clamped with the first portion and the second upper end of the e-liquid suction pipe inserted into the second portion. At least one first protrusion is formed on an outer circumference of the first portion and the pumping cover includes at least one first receiving groove clamped with a corresponding at least one first protrusion.

Wherein the piston includes first receiving portion formed at the first lower end thereof, and the pumping head assembly includes a second sealing portion received in the first receiving portion so as to the piston together with the second sealing portion be received in the first portion. The second sealing portion includes a first sealing body, a first central hole passing through the first sealing body, and a pair of first grooves respectively positioned at two opposite ends of the first sealing body.

Wherein the second portion includes a second receiving portion for receiving the first sealing portion therein so as to the second portion, together with the second sealing portion, be received in the e-liquid bottle. The first sealing portion includes a second sealing body, a second central hole passing through the second sealing body, and a second groove positioned on an end of the second sealing body.

Wherein the pumping body includes a first connecting portion extending outward from an outer wall of the receiving room and formed between the first portion and the second portion, an extending direction of the first connecting portion perpendicular to an axis direction of the receiving room. The feeding tube includes a second connecting portion clamped with a corresponding first connecting portion, and the first connecting portion includes a first e-liquid outlet connected to the receiving room. The feeding tube further includes a second e-liquid outlet connected to the first e-liquid outlet.

Wherein the first connecting portion further includes a second protrusion and the second connecting portion includes a second receiving groove arranged thereof corresponding to the second protrusion so as to the first protrusion be fixed in the second receiving groove for installing the feeding tube on the pumping body.

Wherein the pumping head assembly further includes a second elastic element received in the first portion for the first lower end of the piston inserting into the second elastic element.

Wherein the pumping head assembly further includes a steel ball and a compression ring respectively received in the receiving room, the compression ring pressing against the steel ball to seal the steel ball between the e-liquid suction pipe and the compression ring, a lower portion of the second elastic element abutted against the compression ring.

Wherein the e-liquid pumping assembly further includes a ball detent and a PCB assembly. The PCB assembly includes a battery frame connected to the ball detent by an interference fit way, and the housing includes an accommodating slot for receiving an upper portion of the ball detent therein so as to clamp the housing with the battery frame.

An electronic cigarette according to an exemplary embodiment of the present disclosure includes an atomizer, an e-liquid pumping assembly connected to the atomizer for supplying e-liquid to the atomizer. The e-liquid pumping assembly includes a housing, an e-liquid bottle and a pumping head assembly respectively received in the housing. The pumping head assembly includes a piston, a pumping body clamped with the e-liquid bottle by a first sealing portion, a pumping cover clamped with the pumping body, a feeding tube connected to the atomizer and clamped with the pumping body and an e-liquid suction pipe. The piston includes a first upper end exposed outward from the pumping cover and a first lower end inserted into the pumping body. The e-liquid suction pipe includes a second upper end inserted into the pumping body and a second lower end inserted into the e-liquid bottle. The piston is pressed to expel air from the pumping body so that e-liquid can enter the pumping body through the e-liquid suction pipe, while the piston is again pressed for pushing the e-liquid out of the pumping body to enter the atomizer through the feeding tube.

The present disclosure provides the advantages as below.

The structure of the present disclosure is provided that the piston is pressed to expel air from the pumping body so that e-liquid in the e-liquid bottle can enter the pumping body through the e-liquid suction pipe, thereby the e-liquid in the e-liquid bottle can be completely pumped clean. In this way, it can solve those problems of the related art that the e-liquid in the e-liquid bottle can't be completely pumped clean by squeezing the e-liquid bottle.

BRIEF DESCRIPTION OF THE DRAWINGS

Many aspects of the embodiments can be better understood with reference to the following drawings. The components in the drawings are not necessarily dawns to scale, the emphasis instead being placed upon clearly illustrating the principles of the embodiments. Moreover, in the drawings, like reference numerals designate corresponding parts throughout the several views.

DETAILED DESCRIPTION

Figure 1:
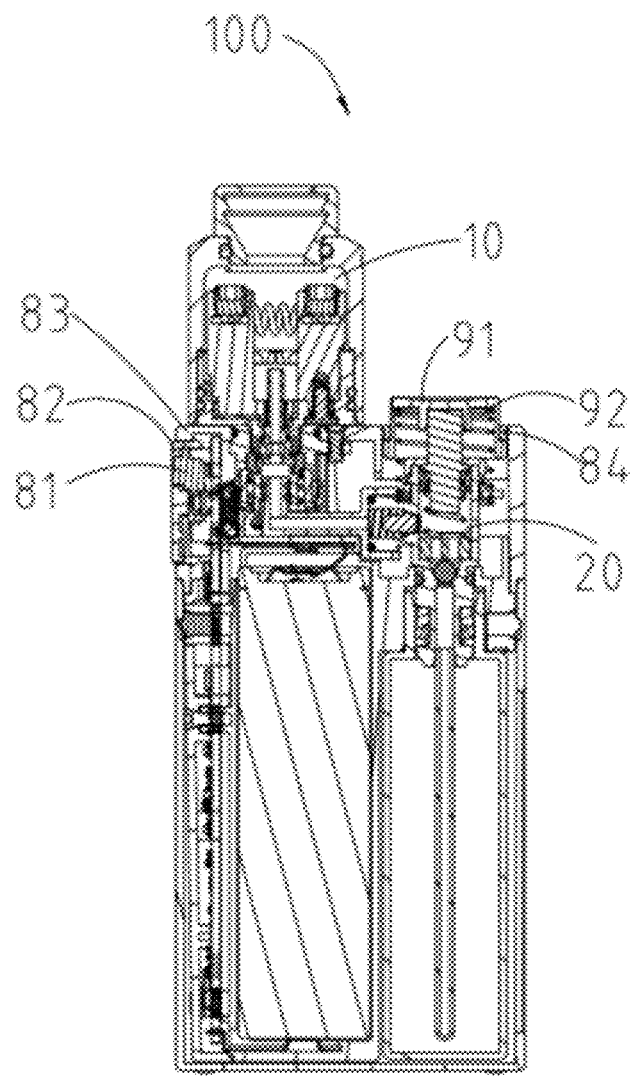
FIG. 1 is a cross-sectional view of the electronic cigarette in accordance with an exemplary embodiment.

The disclosure is illustrated by way of example and not by way of limitation in the figures of the accompanying drawings, in which like reference numerals indicate similar elements.

Figure 2:
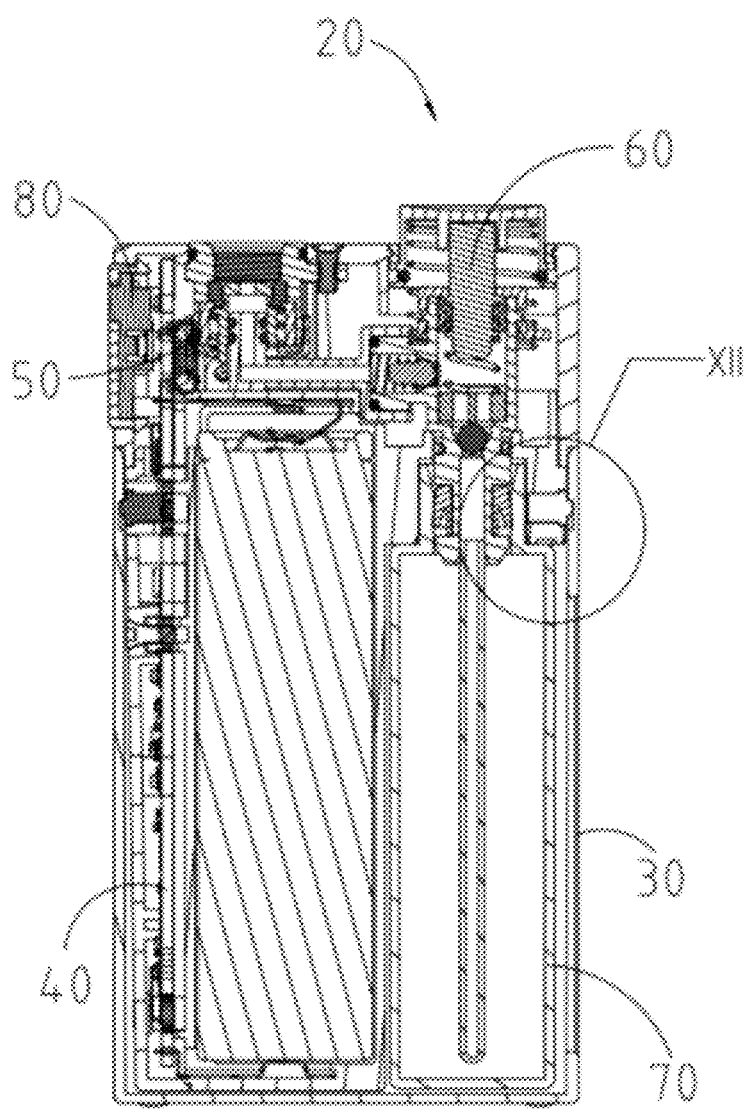
FIG. 2 is a cross-sectional view of an e-liquid pumping assembly of the electronic cigarette FIG. 1.

Referring to FIGS. 1 & 2, the electronic cigarette 100 in accordance with an exemplary embodiment of the present disclosure includes an atomizer 10 and an e-liquid pumping assembly 20. The atomizer 10 is installed on the e-liquid pumping assembly 20 and the e-liquid pumping assembly 20 is configured to supply e-liquid for the atomizer 10.

Figure 3:
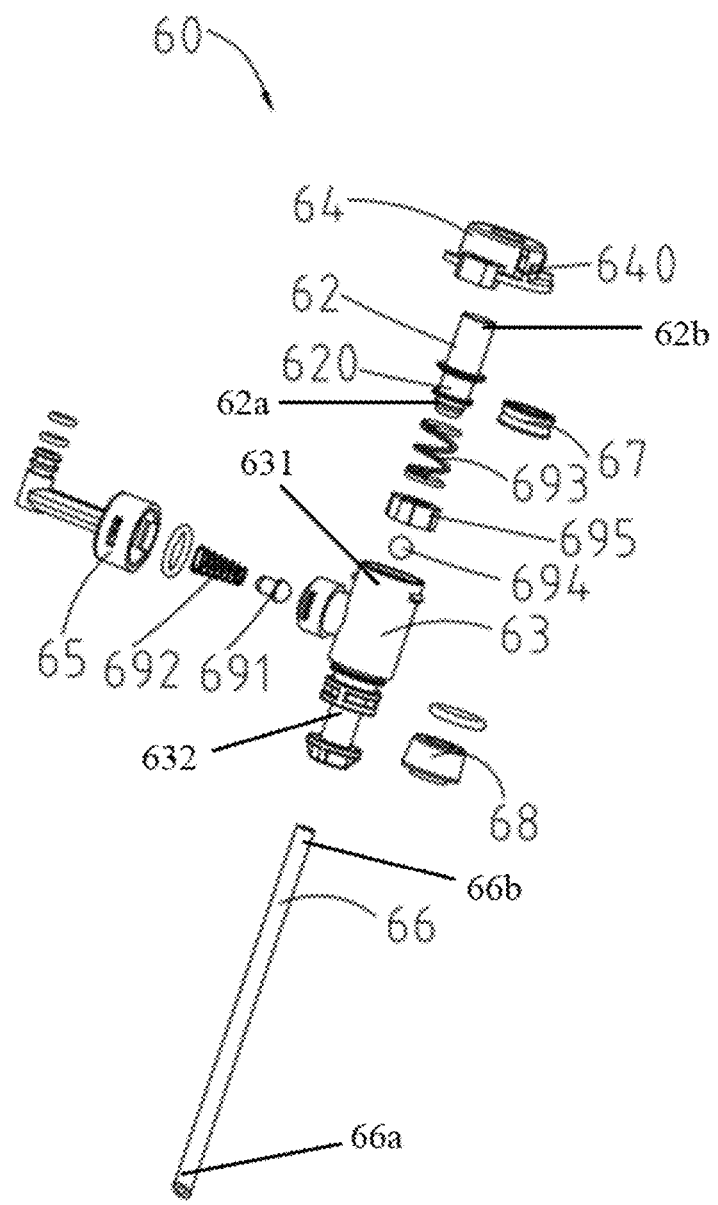
FIG. 3 is an exploded, schematic view of a pumping head assembly of the electronic cigarette of FIG. 1.
Figure 4:
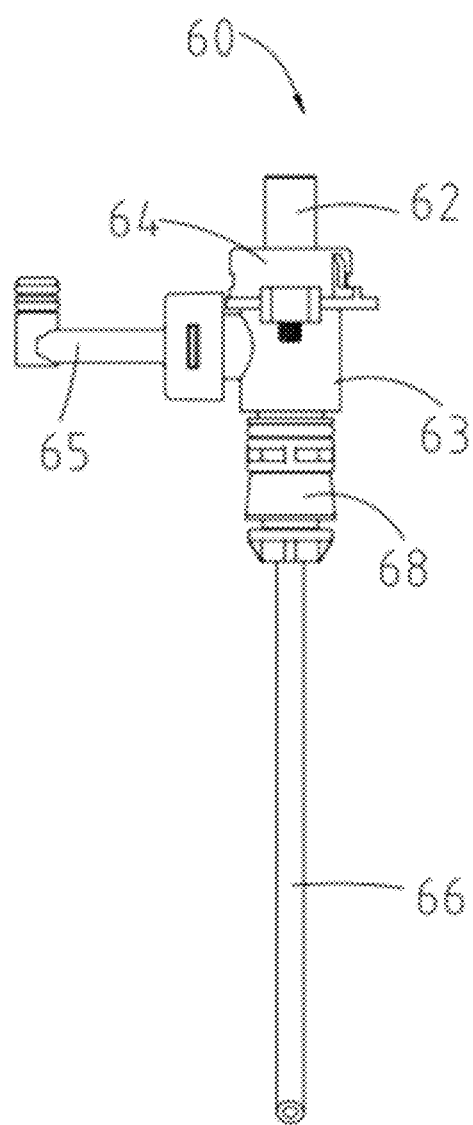
FIG. 4 is an assembly schematic view of the pumping head assembly of FIG. 3.
Figure 5:
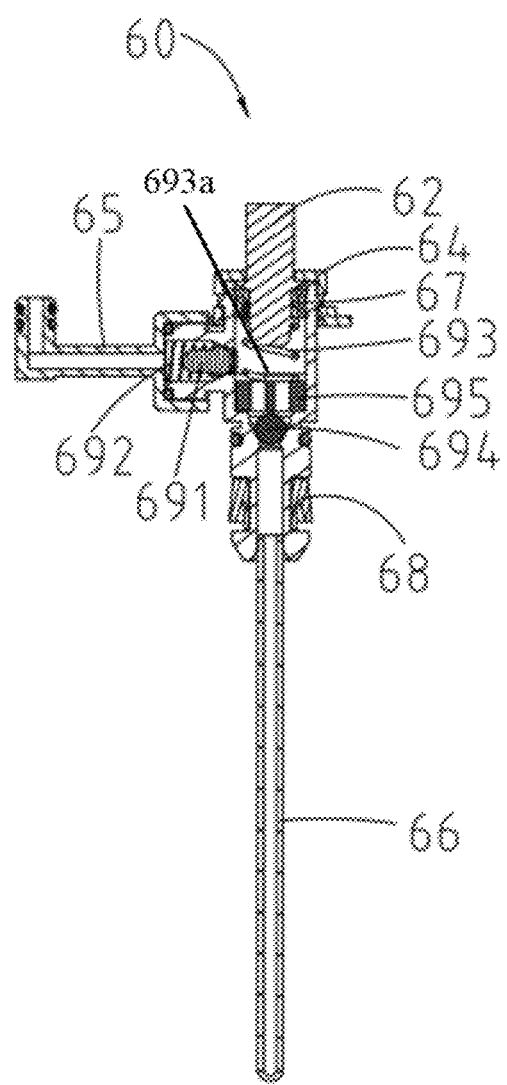
FIG. 5 is a cross-sectional of the pumping head assembly of FIG. 4.

Referring to FIGS. 1-3, the e-liquid pumping assembly 20 includes a housing 30, a PCB assembly 40, an electrode assembly 50, a pumping head assembly 60 and an e-liquid bottle 70. All of the PCB assembly 40, the electrode assembly 50 and the pumping head assembly 60 are received in the housing 30, the PCB assembly 40 is connected to the electrode assembly 50 and the pumping head assembly 60. The pumping head assembly 60 includes a piston 62, a pumping body 63, a pumping cover 64, a feeding tube 65 and an e-liquid suction pipe 66. The feeding tube 65 is connected to the atomizer 10 and clamped with the pumping body 63. The piston 62 includes a first lower end 62a inserted into the pumping body 63 and a first upper end 62b exposed outward from the pumping cover 64. The e-liquid suction pipe 66 includes a second lower end 66a inserted into the e-liquid bottle 70 and a second upper end 66b inserted into the pumping body 63. The pumping body 63 is clamped with the e-liquid bottle 70 and the pumping cover 64 is clamped with the pumping body 63. The piston 62 is pressed to expel air from the pumping body 63 so that e-liquid can enter the pumping body 63 through the e-liquid suction pipe 66; while the piston 62 is again pressed for pushing the e-liquid out of the pumping body 63 to enter the atomizer 10 through the feeding tube 65.

The piston 62 is pressed to expel air from the pumping body 63 so that e-liquid in the e-liquid bottle 70 can enter the pumping body 63 through the e-liquid suction pipe 66, thereby the e-liquid in the e-liquid bottle 70 can be completely pumped clean. In this way, it can solve that problems of the related art that the e-liquid in the e-liquid bottle 70 can't be completely pumped clean by squeezing the e-liquid bottle 70.

Furthermore, the pumping body 63 is clamped with each of the feeding tube 65, the pumping cover 64 and the e-liquid bottle 70, thereby the pumping head assembly 60 can be conveniently assembly or disassembly from the e-liquid pumping assembly 20. That is to say, the assembly mode of the pumping head assembly 60 is a rigid fastening connection, which is convenient for the overall assembly and placement, and the installation is more convenient and reliable.

Referring to FIGS. 3-7, the pumping body 63 is a cylinder-shaped structure and includes a first portion 631, a second portion 632 opposite to the first portion 631 and a receiving room 630 passing through the first portion 631 and die second portion 632. The pumping cover 64 is clamped with the first portion 631 and the second upper end 66b of the e-liquid suction pipe 66 is inserted into the second portion 632. Furthermore, at least one first protrusion 6310 is formed on an outer circumference of the first portion 631 and the pumping cover 64 includes at least one first receiving groove 640 clamped with a corresponding at least one first protrusion 6310.

When assembling the pumping head assembly 60, the pumping cover 64 and the pumping body 63 can be assembled together by engaging the first protrusion 6310 with the first receiving groove 640. Otherwise, the pumping cover 64 can be detachable from the pumping body 63 by removing the first protrusion 6310 out of the first receiving groove 640. In this way, the assembly and disassembly of the pumping cover 64 and the pumping body 63 are simple and convenient, thereby improving the convenience of use.

Figure 8:
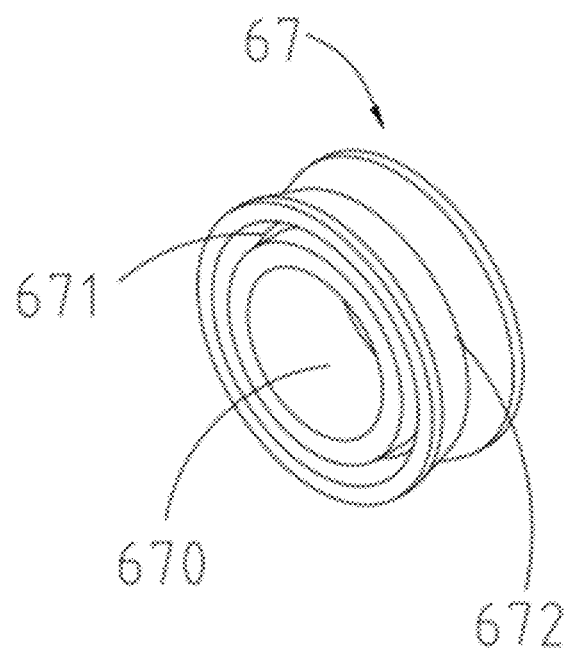
FIG. 8 is a schematic view of a second sealing portion of the pumping head assembly of FIG. 3, but shown from another view.
Figure 9:
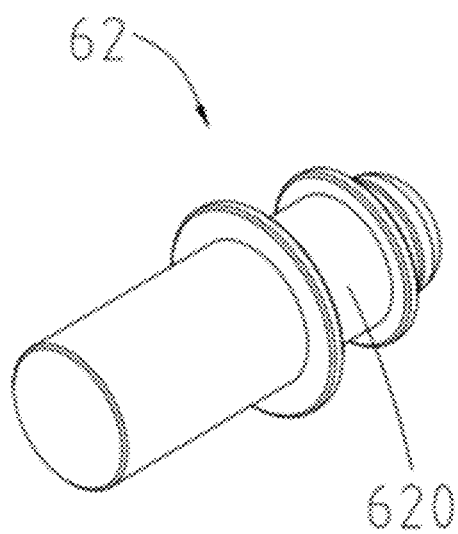
FIG. 9 is a schematic view of a piston of the pumping head assembly of FIG. 3, but shown from another view.
Figure 10:
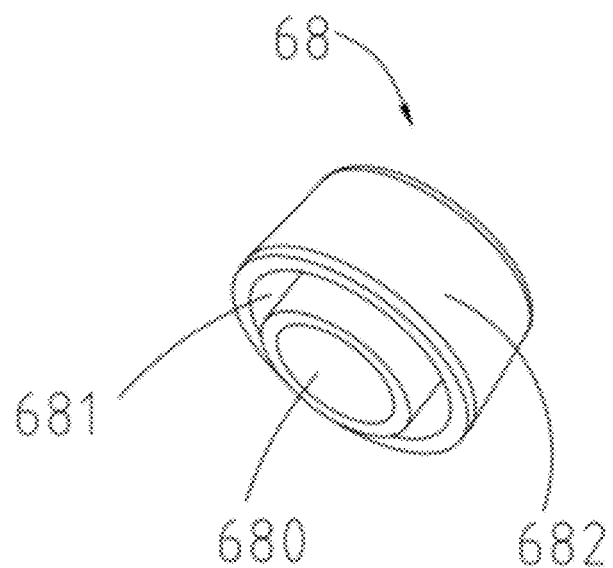
FIG. 10 is a schematic view of a first sealing portion of the pumping head assembly of FIG. 3.

Referring FIG. 8 and FIG. 9, in an exemplary embodiment of the present disclosure, the piston 62 is a solid configuration and includes a first receiving portion 620 at the first lower end 62a thereof for receiving a second sealing portion 67 therein so that the piston 62 and the second sealing portion 67 are received in the first portion 631. When the piston 62 is installed on the first portion 631 of the pumping body 63, both the piston 62 and the first portion 631 are sealed by the second sealing portion 67, thereby an inner tightness of the pumping body 63 is enhanced.

The cross-sectional of the second sealing portion 67 is approximately V-shaped structure and includes a first sealing body 672, a first central hole 670 passing through the first sealing body 672, and a pair of first grooves 671 respectively positioned at two opposite ends of the first sealing body 672. The cross-sectional of the second sealing portion 67 is approximately V-shaped structure.

Because the pair of the first grooves 671 is arranged on two opposite ends of the first sealing portion 672, in the process of installation, the first sealing body 672 can contract towards the first central hole 670 so that the second sealing portion 67 can be easily instilled on the first portion 631 of the pumping body 63. After installation, the first sealing body 672 can expand backward to the first central hole 670, thereby enhancing the sealing performance between the piston 62 and the pumping body 63.

Referring to FIGS. 2-3, FIG. 6 and FIG. 10, the second portion 632 includes a second receiving portion 6320 and the pumping head assembly 60 includes a first sealing portion 68 received in the second receiving portion 6320 so as to the second portion 632, together with the second sealing portion 67, be received in the e-liquid bottle 70. The first sealing portion 68 includes a second sealing body 682, a second central hole 680 passing through the second sealing body 682, and a second groove 681 positioned on an end of the second sealing body 682.

In an exemplary embodiment of the present disclosure, the cross-sectional of the second groove 681 is approximately V-shaped structure. When the second portion 632 is received in the e-liquid bottle 70, the second sealing body 682 can contract towards the second central hole 680. After installation, the second sealing body 682 can expand backward to the second central hole 680, thereby enhancing the sealing performance between an inner wall of the e-liquid bottle 70 and the pumping body 63. When disassembled, the pumping body 63 and the e-liquid bottle 70 can be separated by squeezing the second sealing body 682 towards the second central hole 680. That is to say, because the first sealing portion 68 is provided with a V-shaped second groove 681, the installation and detachable connection between the pumping body 63 and the e-liquid bottle 70 is more easier, thereby the problem of inconvenient replacement of the related art can be solved. At the same time, the V-shaped second groove 681 is formed at one end of the first sealing portion 68 so that the first sealing portion 68 has a certain rebound force to better seal the e-liquid bottle 70 and the pumping body 63. In other words, the pumping body 63 and the e-liquid bottle 70 can be reliably connected to each other by the first sealing portion 68.

During installation, the opening of the second groove 681 faces towards the e-liquid bottle 70, that is, the opening of the V-shaped second groove 681 faces down, and the other opposite end of the second sealing body 682 does not have a V-shaped groove. Therefore, the e-liquid in the e-liquid bottle 70 can't flow back into the pumping body 63 due to a return gas, which can prevent gas from returning under without one-way valve, reduce the manufacturing cost and improve the convenience of use.

Figure 6:
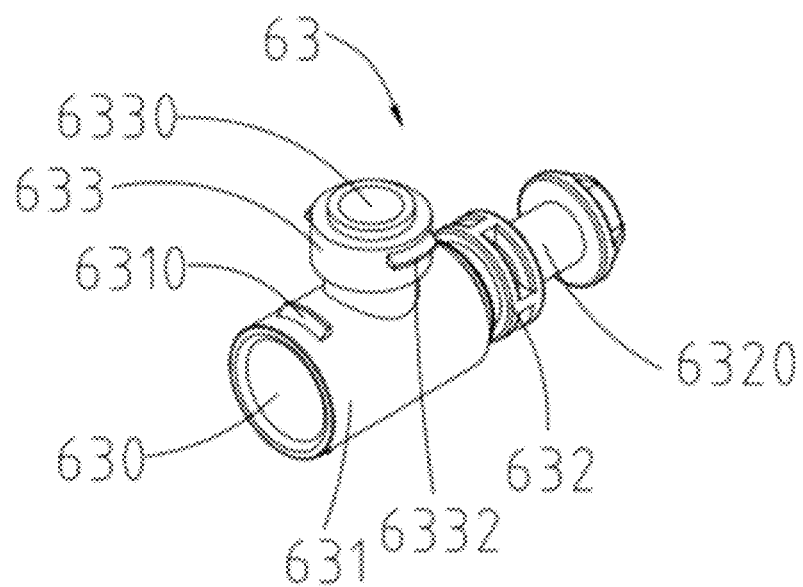
FIG. 6 is a schematic view of a pumping body of the pumping head assembly of FIG. 3, but shown from another view.
Figure 7:
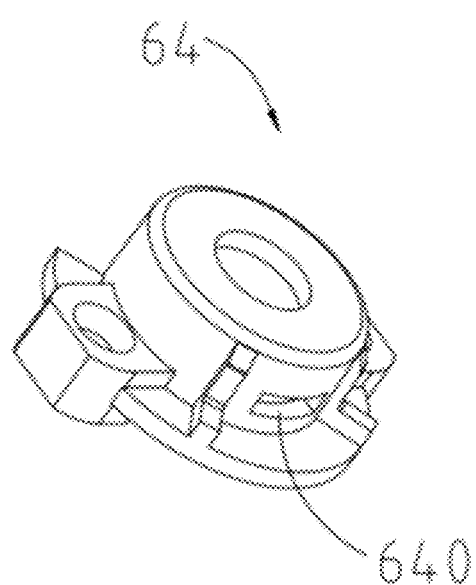
FIG. 7 is a schematic view of a pumping cover of the pumping head assembly of FIG. 3.
Figure 11:
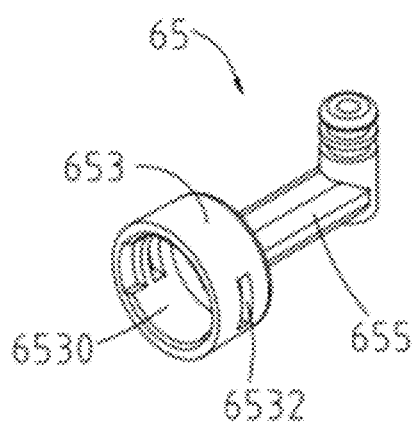
FIG. 11 is a schematic view of a first sealing portion of the pumping head assembly of FIG. 3, but shown from another view.

Referring to FIG. 3, FIG. 6 and FIG. 11, the pumping body 63 includes a first connecting portion 633 extending outward from an outer wall of the receiving room 630 and formed between the first portion 631 and the second portion 632, with an extending direct of the first connecting portion 633 perpendicular to an axis direction of the receiving room 630. The feeding tube 65 includes a second connecting portion 653 clamped with a corresponding first connecting portion 633.

Furthermore, the first connecting portion 633 includes a first e-liquid outlet 6330 perpendicularly connected to the receiving room 630. The feeding tube 65 further includes a second e-liquid outlet 6530 coaxially connected to the first e-liquid outlet 6330.

Furthermore, the first connecting portion 633 further includes a second protrusion 6332 and the second connecting portion 653 includes a second receiving groove 6532 arranged thereof corresponding to the second protrusion 6332 so as to the first protrusion 6310 be fixed in the second receiving groove 6532 for installing the feeding tube 65 on the pumping body 63.

Furthermore, the feeding tube 65 further includes a connecting tube 655 and the second connecting portion 653 is positioned on an end of the connecting tube 655, an opposite end of the connecting tube 655 is connected to the atomizer 10. A cross-sectional of the connecting tube 655 is L-shaped structure.

Referring to FIG. 3, the pumping head assembly 60 includes a key valve 691 installed within the first connecting portion 633, and a first elastic element 692 sleeved around the key valve 691.

Furthermore, the pumping head assembly 60 further includes a second elastic element 693 received in the first portion 631 for the first lower end 62*a* of the piston 62 inserting into the second elastic element 693.

In an exemplary embodiment of the present disclosure, both the first elastic element 692 and the second elastic element 693 are spring.

Furthermore, the pumping head assembly 60 further includes a steel ball 694 and a compression ring 695 respectively received in the receiving room 630. The steel ball 694 is sealed between the e-liquid suction pipe 66 and the compression ring 695 by the compression ring 695 pressing against the steel ball 694, and a lower portion 693*a* of the second elastic element 693 is abutted against the compression ring 695.

Referring to FIGS. 1-3, the e-liquid pumping assembly 20 further includes a cover member 80. The cover member 80 includes a key pad 81, a key cap 82, an upper cover 83 and an anti-scratch ring 84. The key pad 81 is caught into the key cap 82 by an interference fit way, and then the key cap 82 is stuck on the upper cover 83, finally the anti-scratch 84 is stuck on the upper cover 83 by a loop buckle way. The e-liquid pumping assembly 20 further includes a pumping key cap 91 received in the upper cover 83 through a clearance fit way and limited by the anti-scraping ring 84, and a third elastic element 92 sleeved around the piston 62. The pumping key cap 91 covers an upper surface of the piston 62 to press against the piston 62. In the process of pressing the piston 62, the third elastic element 92 can supply a spring force to help the piston 62 reset.

Because the pumping key cap 91 is equipped with the anti-scratch ring 84 to prevent the pumping key cap 91 from being painted. At the same time, the third elastic element 92 is attached to the pumping key cap 91 on the outside of the piston 62 so that the piston 62 can be pressed with a better grip.

Figure 12:
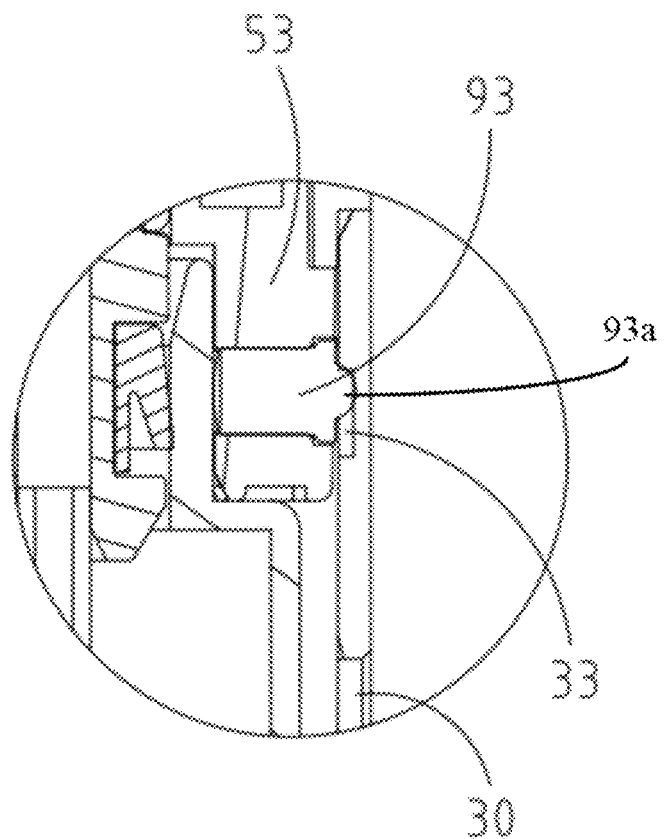
FIG. 12 is an enlarged view of circle XII of FIG. 2.

Referring to FIG. 2 and FIG. 12, the housing 30 includes a accommodating slot 33 and the e-liquid pumping assembly 20 further includes a ball detent 93. The PCB assembly 40 includes a battery frame 53 connected to the ball detent 93 by an interference fit way, and the accommodating slot 33 is provided for receiving an upper portion 93*a* of the ball detent 93 therein so as to clamp the housing 30 with the battery frame 53.

Because the battery frame 53 is connected to the housing 30 by means of the ball detent 93, which is more convenient to replace a battery.

Referring to FIGS. 1-12, during installation, the pumping head assembly 60 is connected to the PCB assembly 40 through fastening screws, the electrode assembly 50 is mounted on the feeding tube 65 of the pumping head assembly 60 through a hollow electrode. The PCB assembly 40 is fixed to the electrode assembly 50, together with the pumping head assembly 60, which are received in the housing 30. The electrode assembly 50 is fixed to the cover member 80 and the cover member 80 is fixed to the housing 30. In this way, the cover member 80, the housing 30, the PCB assembly 40, the electrode assembly 50 and the pumping head assembly 60 are assembled together to obtain the e-liquid pumping assembly 20. The atomizer 10 is then connected to the pumping head assembly 60, thereby the electronic cigarette 100 is obtained.

When the electronic cigarette 100 is used, the pumping key cap 91 is first pressed so that the piston 62 can compress an inner space of the pumping body 63. Secondly, the key valve 691 is opened to expel air from the pumping body 63 and the piston 62 is released and reset. At this time, the key valve 691 is closed and the steel ball 694 is sucked up, the e-liquid in the e-liquid bottle 70 is then sucked into the pumping body 63 through the e-liquid suction pipe 66. Furthermore, the piston 62 is again pressed and the key valve 691 is again opened so that the e-liquid is squeezed out of the pumping body 63 and enters the atomizer 10 through the feeding tube 65.

Although the features and elements of the present disclosure are described as embodiments in particular combinations, each feature or element can be used alone or in other various combinations within the principles of the present disclosure to the full extent indicated by the broad general meaning of the terms in which the appended claims are expressed.

What is claimed is:

1. An e-liquid pumping assembly for supplying e-liquid to an atomizer, comprising a housing, an e-liquid bottle, and a pumping head assembly with the e-liquid bottle respectively received in the housing; the pumping head assembly comprising a piston, a pumping body clamped with the e-liquid bottle by a first sealing portion, a pumping cover clamped with the pumping body, a feeding tube connected to the atomizer and clamped with the pumping body, and an e-liquid suction pipe;

the piston comprising a first upper end exposed outward from the pumping cover and a first lower end inserted into the pumping body;

the e-liquid suction pipe comprising a second upper end inserted into the pumping body and a second lower end inserted into the e-liquid bottle; and wherein the piston is pressed to expel air from the pumping body so that e-liquid can enter the pumping body through the e-liquid suction pipe; while the piston is again pressed for pushing the e-liquid out of the pumping body to enter the atomizer through the feeding tube.

2. The e-liquid pumping assembly as claimed in claim 1, wherein the pumping body comprises a first portion, a second portion opposite to the first portion and a receiving room passing through the first portion and the second portion, the pumping cover clamped with the first portion and the second upper end of the e-liquid suction pipe inserted into the second portion; at least one first protrusion formed on an outer circumference of the first portion and the pumping cover comprising at least one first receiving groove clamped with a corresponding at least one first protrusion.

3. The e-liquid pumping assembly as claimed in claim 2, wherein the piston comprises a first receiving portion formed at the first lower end thereof, and the pumping head assembly comprises a second sealing portion received in the first receiving portion so as to the piston together with the second sealing portion be received in the first portion; the second sealing portion comprising a first sealing body, a first central hole passing through the first sealing body, and a pair of first grooves respectively positioned at two opposite ends of the first sealing body.

4. The e-liquid pumping assembly as claimed in claim 2, wherein the second portion comprises a second receiving portion for receiving the first sealing portion therein so as to the second portion together with the second sealing portion be received in the e-liquid bottle; the first sealing portion comprising a second sealing body, a second central hole passing through the second sealing body, and a second groove positioned on an end of the second sealing body.

5. The e-liquid pumping assembly as claimed in claim 2, wherein the pumping body comprises a first connecting portion extending outward from an outer wall of the receiving room and formed between the first portion and the second portion, an extending direction of the first connecting portion perpendicular to an axis direction of the receiving room, the feeding tube comprising a second connecting portion clamped with a corresponding first connecting portion, and the first connecting portion comprising a first e-liquid outlet connected to the receiving room, the feeding tube further comprising a second e-liquid outlet connected to the first e-liquid outlet.

6. The e-liquid pumping assembly as claimed in claim 5, wherein the first connecting portion further comprises a second protrusion and the second connecting portion comprises a second receiving groove arranged thereof corresponding to the second protrusion so as to the first protrusion be fixed in the second receiving groove for installing the feeding tube on the pumping body.

7. The e-liquid pumping assembly as claimed in claim 2, wherein the pumping head assembly further comprises a second elastic element received in the first portion for the first lower end of the piston inserting into the second elastic element.

8. The e-liquid pumping assembly as claimed in claim 7, wherein the pumping head assembly further comprises a steel ball and a compression ring respectively received in the receiving room, the steel ball sealed between the e-liquid suction pipe and the compression ring by the compression pressing against the steel ball, a lower portion of the second elastic element abutted against the compression ring.

9. The e-liquid pumping assembly as claimed its claim 1, wherein the e-liquid pumping assembly further comprises a ball detent and a PCB assembly comprising a battery frame connected to the ball detent by an interference fit way, the housing comprising an accommodating slot for receiving an upper portion of the ball detent therein so as to clamp the housing with the battery frame.

10. An electro cigarette comprising:
an atomizer;
an e-liquid pumping assembly connected to the atomizer for supplying e-liquid to the atomizer and comprising a housing, an e-liquid bottle and a pumping head assembly respectively received in the housing;
the pumping head assembly comprising a piston, a pumping body clamped with the e-liquid bottle by a first sealing portion, a pumping cover clamped with the pumping body, a feeding tube connected to the atomizer and clamped with the pumping body and an e-liquid suction pipe;
the piston comprising a first upper end exposed outward from the pumping cover and a first lower end inserted into the pumping body;
the e-liquid suction pipe comprising a second upper end inserted into the pumping body and a second lower end inserted into the e-liquid bottle; and wherein the piston is pressed to expel air from the pumping body so that e-liquid can enter the pumping body through the e-liquid suction pipe; while the piston is again pressed for pushing the e-liquid out of the pumping body to enter the atomizer through the feeding tube.

11. The electronic cigarette as claimed in claim 10, wherein the pumping body comprises a first portion, a second portion opposite to the first portion and a receiving room passing through the first portion and the second portion, the pumping cover clamped with the first portion and the second upper end of the e-liquid suction pipe inserted into the second portion; at least one first protrusion formed on an outer circumference of the first portion and the pumping cover comprising at least one first receiving groove clamped with a corresponding at least one first protrusion.

12. The electronic cigarette as claimed in claim 11, wherein the piston comprises a first receiving portion formed at the first lower end thereof, and the pumping head assembly comprises a second sealing portion received in the first receiving portion so as to the piston together with the second sealing portion be received in the first portion; the second sealing portion comprising a first sealing body; a first central hole passing through the first sealing body, and a pair of first grooves respectively positioned at two opposite ends of the first sealing body.

13. The electronic cigarette as claimed in claim 11, wherein the second portion comprises a second receiving portion for receiving the first sealing portion therein so as to the second portion together with the second sealing portion be received in the e-liquid bottle; the first sealing portion comprising a second sealing body, a second central hole passing through the second sealing body, and a second groove positioned on an end of the second sealing body.

14. The electronic cigarette as claimed in claim 11, wherein the pumping body comprises a first connecting portion extending outward from an outer wall of the receiving room and formed between the first portion and the second portion, an extending direction of the first connecting portion perpendicular to an axis direction of the receiving room, the feeding tube comprising a second connecting portion clamped with a corresponding first connecting portion, and the first connecting portion comprising a first e-liquid outlet connected to the receiving room, the feeding tube further comprising a second e-liquid outlet connected to the first e-liquid outlet.

15. The electronic cigarette as claimed in claim 14, wherein the first connecting portion further comprises a second protrusion and the second connecting portion comprises a second receiving groove arranged thereof corresponding to the second protrusion so as to the first protrusion be fixed in the second receiving groove for installing the feeding tube on the pumping body.

16. The electronic cigarette as claimed in claim 11, wherein the pumping head assembly further comprises a second elastic element received in the first portion for the first lower end of the piston inserting into the second elastic element.

17. The electronic cigarette as claimed in claim 16, wherein the pumping head assembly further comprises a steel ball and a compression ring respectively received in the receiving room, the steel ball sealed between the e-liquid suction pipe and the compression ring by the compression ring pressing against the steel ball, a lower portion of the second elastic element abutted against the compression ring.

18. The electronic cigarette as claimed in claim 10, wherein the e-liquid pumping assembly further comprises a ball detent and a PCB assembly comprising a battery frame connected to the ball detent by an interference fit way, the housing comprising an accommodating slot for receiving an upper portion of the ball detent therein so as to clamp the housing with the battery frame.

* * * * *